United States Patent [19]

Drake

[11] Patent Number: 4,952,741

[45] Date of Patent: Aug. 28, 1990

[54] PARAFFINIC MATERIAL TREATMENT FOR CATALYSTS AND OLEFIN DIMERIZATION PROCESSES THEREWITH

[75] Inventor: Charles A. Drake, Nowata, Okla.

[73] Assignee: Phillips Petroleum Company, Bartlesville, Okla.

[21] Appl. No.: 465,712

[22] Filed: Jan. 16, 1990

Related U.S. Application Data

[62] Division of Ser. No. 233,094, Aug. 17, 1988.

[51] Int. Cl.$^5$ .............................................. C07C 2/24
[52] U.S. Cl. .................................................. 585/516
[58] Field of Search ........................................ 585/516

[56] References Cited

U.S. PATENT DOCUMENTS

| | | | |
|---|---|---|---|
| 1,390,683 | 9/1921 | Ellis | 502/173 |
| 2,818,350 | 12/1957 | Kavanagh | 117/100 |
| 2,986,588 | 5/1961 | Schramm | 260/683.15 |
| 3,175,020 | 3/1965 | Wilkes | 260/683.15 |
| 3,216,947 | 11/1965 | Wilkes | 252/192 |
| 3,563,912 | 2/1971 | Young | 502/150 X |
| 3,720,627 | 3/1973 | Jarvis | 252/430 |
| 3,849,334 | 11/1974 | Frielingsdorf et al. | 252/429 B |
| 3,916,019 | 10/1975 | Closson et al. | 260/683.15 E |
| 4,388,480 | 6/1983 | Imai et al. | 585/516 |
| 4,609,637 | 9/1986 | Drake | 502/174 |
| 4,656,154 | 4/1987 | Drake | 502/185 |

OTHER PUBLICATIONS

The Condensed Chemical Dictionary, Pub. by Reinhold Pub. Corp., N.Y., NY, 5th Ed (1956), pp. 40, 888, & 991.

Primary Examiner—H. M. S. Sneed
Assistant Examiner—J. Saba
Attorney, Agent, or Firm—Lynda S. Jolly

[57] ABSTRACT

Catalyst supports, catalyst systems, methods for the preparation thereof, and dimerization process therewith are provided. Catalyst systems comprise at least one elemental alkali metal and at least one paraffinic material deposited on an alkali metal carbonate catalyst support. Optionally, the catalyst system further comprises at least one promoter and at least one carbonaceous compound.

18 Claims, No Drawings

PARAFFINIC MATERIAL TREATMENT FOR CATALYSTS AND OLEFIN DIMERIZATION PROCESSES THEREWITH

This application is a division of application Ser. No. 07/233,094, filed Aug. 17, 1988.

BACKGROUND OF THE INVENTION

It is known in the art to employ alkali metal carbonate supported elemental alkali metal catalysts for such conversions as propylene dimerization. Several methods of preparing these types of catalysts are known in the art. The resultant catalyst usually contains some exposed elemental alkali metal. However, elemental alkali metals are unstable at standard temperature, pressure, and atmosphere conditions. Thus, these catalysts usually must be stored under a dry, inert atmosphere. Furthermore, known processes to prepare these types of catalysts can result in uneven distribution of the elemental alkali metal on the catalyst support. Additionally, known processes to prepare these types of catalysts can produce a congealed catalyst mass that can be difficult to handle.

SUMMARY OF THE INVENTION

It is an object of this invention to provide an improved catalyst system for the dimerization of olefins.

It is another object of this invention to provide a method to prepare an improved alkali metal carbonate supported elemental alkali metal catalyst system.

It is yet another object of this invention to provide an improved process for the dimerization of olefins.

In accordance with this invention, a dimerization catalyst comprising at least one elemental alkali metal on an alkali metal carbonate support is treated with at least one paraffinic material. The resultant treated catalyst can be stored at standard temperature and pressure conditions under any atmosphere.

DESCRIPTION OF THE PREFERRED EMBODIMENTS

Supports

The catalyst support can be formed by any method known in the art. Thus, commercially available alkali metal carbonate in the form of powder, pellets, granules, or any other form can be treated directly with at least one elemental alkali metal and, optionally, one or more of the desired promoting materials as discussed more fully below. This form of support has the advantage of being most readily obtained with a minimum of handling.

In some circumstances, a large particle size and/or more rugged form of catalyst support is desired, such as, for example, where fixed bed reactions, especially large volume fixed bed reactions, are carried out. One particular technique for support preparation is to form a thick paste comprising alkali metal carbonate and water; alkali metal carbonate, water, and alcohol; or alkali metal carbonate, water, and water soluble ketone. The thick paste can be extruded, pelletized, pilled, or tabletted into appropriate sizes. The resultant material is then oven dried under conditions of time and temperature to insure that substantially all liquid is driven off. These types of supports will be referred to as "wet process" alkali metal carbonate supports.

Alcohols suitable for use in preparation of "wet process" catalyst supports are straight chain and branched aliphatic alcohols having from about 1 to about 7 carbon atoms. Water soluble ketones suitable for use in preparation of "wet process" catalyst supports are straight chain and branched water soluble ketones having from about 3 to about 7 carbon atoms.

In accordance with another technique for the support preparation alkali metal carbonate can be mixed with a non-acidic inorganic oxide and/or finely divided stainless steel. The mixture is heated to at least 950° C., then cooled, and finally, if desired, broken into pieces or fractionated to a desired particle size. Catalyst support prepared in this manner will be referred to as "melt process" alkali metal carbonate supports.

Suitable non-acidic inorganic oxides include, but are not limited to, alumina, such as alpha-alumina, silica, silica-alumina, magnesia-titania, thoria, magnesia, titania, zirconia, and mixtures of two or more thereof. Stainless steel as used herein is intended to cover broadly those alloys of iron which are relatively inert to the reaction conditions employed for olefin dimerization.

In accordance with another technique for the support preparation, an alkali metal carbonate is pelletized with at least one carbonaceous compound. The pelleted support, either as pellets or as smaller crushed particles, is then heated in an oxygen-containing atmosphere under conditions suitable to oxidize in the range of about 10 to about 90 weight percent of the carbonaceous compound. As a result of this partial oxidation of the pelleted support, the concentration of carbonaceous compound remaining on the surface of the support is substantially less than the concentration of carbonaceous compound remaining on the interior portions of the support. Catalyst support prepared in this manner will be referred to as "carbon containing" alkali metal carbonate support.

The term "carbonaceous compound" is intended to include various forms of the element carbon. Examples include, but are not limited to, carbon black, charcoal, coconut charcoal, amorphous graphite, and crystallite graphite.

Once the catalyst support is formed, it should be calcined in an oxygen-containing atmosphere at a temperature in the range of about 80° to about 350° C., preferably about 250° C., for a time of at least 2 hours. Times in excess of about 20 hours generally impart no additional beneficial affect. Thus, times in the range of about 2 to about 20 hours are useful. Upon completion of calcination, the catalyst support can be stored in a dry atmosphere. Preferably, the catalyst support is stored under a dry, oxygen-free atmosphere until needed for further treatment.

Catalysts and Promoters

Catalysts systems employed in the practice of this invention comprise one of the alkali metal carbonate supports described above, at least one elemental alkali metal catalyst, and optionally one or more of the following additional promoters:
 elemental copper,
 elemental cobalt,
 finely divided stainless steel,
 finely divided glass, and
 mixtures of two or more thereof.
It should be recognized, however, that the catalyst systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium and cesium. While the proportion of alkali metal combined with the alkali metal carbonate support can vary appreciably, generally at least about one weight percent of alkali metal based on the total weight of treated support will be employed. Generally, about 1 to about 20 weight percent alkali metal will be employed with about 2 to about 15 weight percent preferred. An alkali metal loading of about 3 to about 10 weight percent based on the total weight of treated support is most preferred for most efficient use of reagents, high catalyst activity and selectivity, and ease of catalyst preparation. Potassium is the preferred elemental alkali metal due to its ready availability as well as ease and safety in handling.

The proportion of optional promoter on the alkali metal carbonate support can vary appreciably, but generally, at least one weight percent of the optional promoter based on the total weight of treated support will be employed. The following amounts are provided for additional guidance:

| Promoter | Loading, Weight Percent | | |
|---|---|---|---|
| | Broad | Intermediate | Preferred |
| Cu | 1–30 | 3–20 | 5–12 |
| Co | 1–50 | 3–25 | 5–15 |
| *SS | 1–80 | 3–60 | 5–50 |
| Glass | 1–50 | 2–25 | 3–15 |

*SS = Stainles Steel

The general procedure for preparation of the catalyst systems, after calcining the support, of the invention involves heating the alkali metal carbonate support to a temperature in the range of about 80° to about 350° C., preferably slightly above the melting point of the particular alkali metal used, cooling the particulate support and then contacting the particulate support with at least one elemental alkali metal in a dry, oxygen-free atmosphere, such as, for example $N_2$, Ar, or the like, at a temperature sufficient to cause the alkali metal to melt. The contacting, done in an oxygen-free atmosphere, is preferably carried out with suitable mixing to ensure even distribution. Suitable temperatures for the contacting step will vary with the particular alkali metal employed. For example, with elemental potassium, temperatures in the range of about 80° to 100° C. are preferred, while with elemental sodium, temperatures in the range of about 100° to 140° C. are preferred.

While the alkali metal treated support is maintained at or above the melting point of the particular alkali metal used, in an oxygen-free atmosphere, any desired promoter(s), such as for example, finely divided stainless steel or elemental copper, can be gradually added while the treated catalyst is continuously stirred. For example, with potassium, temperatures in the range of about 80° to about 100° C. are employed. The catalyst system is then ready to be charged to the reactor.

Optionally, the alkali metal carbonate support, once elemental alkali metal and any desired promoters have been deposited thereon, can be subjected to a subsequent heating step, in an oxygen-free atmosphere, to ensure as uniform a distribution as possible of the various promoters on the surface of the alkali metal carbonate support. Thus, the finished catalyst can be subjected to a temperature in the range of at least about 80° C. for a time in the range of about 0.1 to about 4 hours. A temperature in the range of about 150° to about 250° C. for a time in the range of about 0.5 to about 2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst combinations are possible. Any combination of the alkali metal and optional promoters disclosed can be supported on any alkali metal carbonate support disclosed. Some possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, and conversions desired.

Paraffinic Treatment

After the catalyst has been prepared, it is then treated with at least one paraffinic material. While not wishing to be bound by theory, it is believed that the paraffinic treatment more evenly distributes the elemental alkali metal on the catalyst support, with the added benefit of eliminating the problem of congealing the catalyst into an unmanageable mass. The resultant protective paraffinic material also obviates the need to store the catalyst under an inert atmosphere.

The paraffinic treatment is at a temperature sufficient to maintain both the paraffinic material and elemental alkali metal in a liquid, or molten, state, yet not so high as to destroy or decompose the catalyst and/or paraffinic material. Suitable temperatures for the treating step will vary with the particular paraffinic material and elemental alkali metal employed. For example, if elemental potassium is used, temperatures in the range of about 80° to about 100° C. are preferred, while with elemental sodium, temperatures in the range of about 100° to about 140° C. are preferred.

The paraffinic material can be either a liquid or a solid at room temperature, about 20° C., and atmospheric pressure, about 760 torr, and a liquid at treatment temperatures and pressures. If a liquid paraffinic material is used, it should have appreciable coating action at room temperature. If a solid paraffinic material is used, it should be a liquid at the elemental alkali metal application temperature. Thus, linear or branched aliphatic paraffinic materials with about 8 to about 60 carbon atoms are generally employed. Most preferably, the paraffinic material has from about 10 to about 40 carbon atoms for ease of use. Exemplary paraffinic materials include, but are not limited to, decane, mineral oil (C-16 average carbon number), octadecane, docosane, tetracosane, octacosane, and mixtures thereof. Most preferred paraffinic materials are decane, mineral oil (C-16 average carbon number), docosane, and mixtures thereof because they are inexpensive and readily available. The paraffinic material should also be dry, i.e. water-free, and oxygen-free in order not to adversely affect the catalyst.

According to the invention, the paraffinic material treatment must occur after the elemental alkali metal is put onto the catalyst support. If the paraffinic material is combined with the catalyst support, prior to combining the elemental alkali metal and the catalyst support, the elemental alkali metal will not adhere to the catalyst support.

The catalyst can be at any temperature prior to the paraffinic treatment. Thus, the catalyst can be at room temperature, or the catalyst can be pre-heated, under an inert atmosphere, to the temperature of the paraffinic material. Preferably, to insure even coating and distribution of both the paraffinic material and elemental alkali metal, the catalyst is preheated to the paraffinic treatment temperature.

The time required for the paraffinic treatment is that sufficient to wet, or coat, the catalyst surface. Generally, times in the range of about 3 to about 60 minutes, preferably in the range of about 3 to about 45 minutes, are sufficient. Most preferably, for economy of time and materials, times in the range of about 5 to about 20 minutes are used for sufficient catalyst coating.

The paraffinic treatment can take place under any type of atmosphere. As stated earlier, one of the advantages of the paraffinic treatment is to obviate any need to keep the catalyst under a dry, oxygen-free atmosphere. For ease of use, the paraffinic treatment is done in air.

After the catalyst is sufficiently coated with a paraffinic material, the excess liquid paraffinic material can be decanted off. The treated catalyst, if desired, can be agitated while cooling so that the resultant treated particles are of a manageable particle size.

The treated catalyst can be charged directly to the dimerization reactor or the treated catalyst can be solvent washed prior to use. Preferably, the treated catalyst is solvent washed prior to use to remove the paraffinic material and to avoid possible problems that can be caused by excess paraffinic material in the dimerization reactor. Any suitable hydrocarbon solvent can be used for the wash. Hexane, because of ready availability and ease of use, is preferably employed. Once the paraffinic material is removed from the treated catalyst, the catalyst is preferably stored under a dry, oxygen-free atmosphere.

Reactants

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous types of operation, although the catalysts of the invention are particularly well suited for continuous, fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressure of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

Products

The olefinic products of the invention have established utility in a wide variety of applications such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLE

Catalyst support was prepared by pelleting commerically available anhydrous potassium carbonate on a Stokes-Pennwalt Model 900-511-6 Eureka Tabletting Machine. Pellets (⅛") were prepared and used directly, or crushed and sieved to recover a desirable particle size.

After pelleting, the potassium carbonate pellets (or crushed, sieved material) were subjected to a "burnoff" (oxidation) period in an oxygen-containing atmosphere at a temperature of about 350° C. for a period of about 3 hours.

Following burnoff treatment, the support was allowed to cool, in an oxygen-free atmosphere, to about 80° to about 85° C., at which time, about 5 weight percent, based on the weight of the potassium carbonate, of heptane washed, liquid, elemental potassium was added. Optionally, a paraffinic material was added either before or after the addition of potassium to the potassium carbonate. The catalyst, and optional paraffinic material, was heated to about 100° C. and stirred until the catalyst formed particles, about 10 minutes. If a paraffinic material was added, the mixture was washed with a hydrocarbon solvent; e.g., hexane or heptane. The results are summarized in Table I.

TABLE 1

| Run | Wt. % Paraffinic Material Added | Paraffinic Treatment Before/After Add K | Paraffinic Material | Catalyst Appearance |
|---|---|---|---|---|
| 1 | 0 | not applicable | none | Catalyst solidified into one clump; clump broken up with spatula; some pellets broken |
| 2 | 0 | not applicable | none | Catalyst formed clumps; clumps broken up with spatula, after warming |
| 3 | 80 | after | mineral oil | Catalyst free-flowing; very little coagulation |
| 4 | 50 | after | decane | Catalyst free-flowing |
| 5 | 80 | before | mineral oil | K never adhered to pellets, but made small globules, which became smaller with heating and stirring |

As can be seen from the Catalyst Appearance of Runs 3 and 4, in Table I, use of a paraffinic material enhances the processability of the catalyst. Furthermore, if the paraffinic material is added prior to the addition of the elemental alkali metal, as in Run 5, the potassium does not adhere to the catalyst support; thus, production of the desired catalyst, elemental potassium supported on potassium carbonate, is inhibited.

The example has been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for the dimerization of at least one dimerizable olefin which comprises contacting said olefin under dimerization conditions with a catalyst system comprising:
   (a) at least one elemental alkali metal supported on an alkali metal carbonate support;
   (b) wherein component (a) is then treated with at least one paraffinic material at a temperature sufficient to maintain both said paraffinic material and said elemental alkali metal in a liquid, or molten, state but not sufficient to destroy or decompose said component (a) or said paraffinic material, thereby forming a coated composition.

2. A process according to claim 1 wherein said contacting is carried out at a temperature within the range of about 50° to about 250° C., a pressure within the range of about 100 to about 10,000 psig, and a weight hourly space velocity within a range of about 0.1 to about 10.

3. A process according to claim 1 wherein said elemental alkali metal is potassium.

4. A process according to claim 1 wherein said alkali metal carbonate is potassium carbonate.

5. A process according to claim 1 wherein said paraffinic material is a solid at less than or equal to about 100° C.

6. A process according to claim 5 wherein said paraffinic material is an aliphatic hydrocarbon and has from about 8 to about 60 carbon atoms per molecule.

7. A process according to claim 6 wherein said paraffinic material has from about 10 to about 40 carbon atoms per molecule.

8. A process according to claim 1 wherein said alkali metal carbonate support further comprises at least one carbonaceous compound.

9. A process according to claim 1 wherein said alkali metal carbonate support further comprises at least one inorganic oxide.

10. A process according to claim 1 wherein said catalyst system further comprises a promoter selected from the group consisting of finely divided stainless steel, elemental copper, elemental cobalt, and mixtures thereof.

11. A process for the production of 4-methyl-1-pentene which comprises contacting propylene under dimerization conditions with a catalyst system comprising:
  (a) forming a particulate catalyst support comprising an alkali metal carbonate;
  (b) contacting said particulate catalyst support with an elemental alkali metal to form a catalyst; and
  (c) treating said catalyst with at least one paraffinic material at a temperature sufficient to maintain both said paraffinic material and said elemental alkali metal in a liquid, or molten, state but not sufficient to destroy or decompose said catalyst or said paraffinic material, to form a coated catalyst.

12. A process according to claim 11 wherein said contacting is carried out at a temperature within the range of about 80° to about 200° C., a pressure within the range of about 1,000 to about 4,000 psig, and a weight hourly space velocity within a range of about 0.1 to about 10.

13. A process according to claim 11 wherein said elemental alkali metal is potassium.

14. A process according to claim 11 wherein said alkali metal carbonate is potassium carbonate.

15. A process according to claim 11 wherein said particulate catalyst support further comprises a carbonaceous compound.

16. A process according to claim 11 further comprising contacting said particulate catalyst support with a promoter selected from the group consisting of elemental copper, elemental cobalt, finely divided stainless steel, finely divided glass, and mixtures thereof.

17. A process according to claim 11 wherein said particulate catalyst support is heated at a temperature within the range of about 80° to about 350° C. for a time within the range of about 2 to about 20 hours prior to contacting said elemental alkali metal and said paraffinic material.

18. A process according to claim 11 wherein said paraffinic material is an aliphatic hydrocarbon and has from about 8 to about 60 carbon atoms per molecule.

* * * * *